United States Patent
Ostroff (10) Patent No.: US 8,666,489 B2
(45) Date of Patent: Mar. 4, 2014

(54) DEVICES FOR TACHYARRHYTHMIA SENSING AND HIGH-PASS FILTER BYPASS

(75) Inventor: Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 30 days.

(21) Appl. No.: 13/358,015

(22) Filed: Jan. 25, 2012

(65) Prior Publication Data

US 2012/0123488 A1 May 17, 2012

Related U.S. Application Data

(62) Division of application No. 11/197,137, filed on Aug. 4, 2005, now Pat. No. 8,116,867.

(51) Int. Cl.
*A61N 1/362* (2006.01)

(52) U.S. Cl.
USPC .................. 607/14; 607/25; 600/515

(58) Field of Classification Search
USPC ............ 607/91, 11, 14, 15, 25; 600/508, 509, 600/513–518; 128/902
See application file for complete search history.

(56) References Cited

U.S. PATENT DOCUMENTS 7,274,959 B1 * 9/2007 Wang et al. .................. 600/509

* cited by examiner

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

The present invention, in illustrative embodiments, includes devices for analyzing cardiac signals in an implantable cardiac stimulus system. Within the analysis, a threshold may be defined related to a cardiac event rate. If the cardiac event rate does not exceed the threshold, filtering of captured cardiac signals occurs, including attenuating T-waves. If the cardiac event rate does exceed the threshold, circuitry for analog filtering or programming for digital filtering is bypassed to avoid attenuating low frequency components of the captured cardiac signals.

16 Claims, 7 Drawing Sheets

DEVICES FOR TACHYARRHYTHMIA SENSING AND HIGH-PASS FILTER BYPASS

RELATED APPLICATIONS

The present application is a divisional of U.S. patent application Ser. No. 11/197,137, filed Aug. 4, 2005, and published as US Patent Application Publication Number 2007-0032829 on Feb. 8, 2007, now U.S. Pat. No. 8,116,867, the entire disclosure of which is incorporated herein by reference.

FIELD

The prevent invention is related to the field of implantable medical devices. More particularly, the present invention relates to cardiac signal analysis in the field of implantable cardiac stimulus devices.

BACKGROUND

Beat detection is one feature used in implantable cardiac stimulation devices. Accurate beat detection is important to ensuring device success. For example, with an implantable cardioverter/defibrillator (ICD), inaccurate beat detection can lead to unnecessary stimulus and/or failure to provide stimulus when needed.

Figure 1:
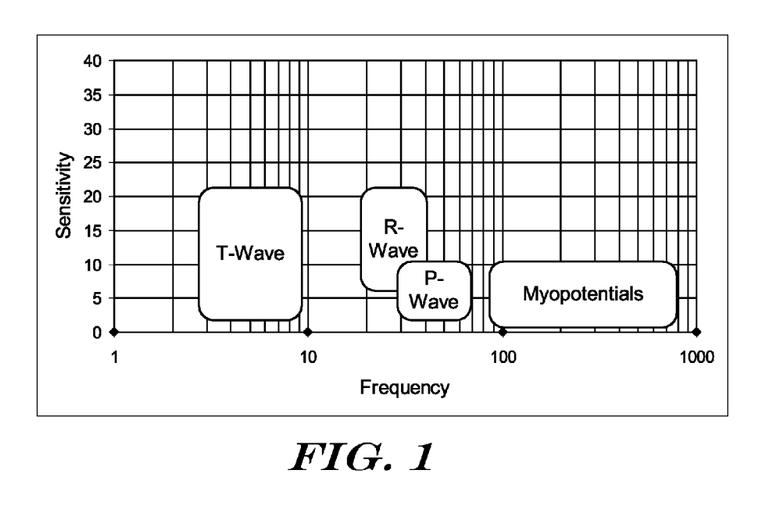
FIG. 1 is a logarithmic plot illustrating frequency content of certain biometric signals.

FIG. 1, taken from Ellenbogen et al. in CLINICAL CARDIAC PACING AND DEFIBRILLATION $2^{ND}$ Ed. (W.B. Saunders Co. 2000), at 201, shows that the frequency content of raw cardiac signals includes various components. T-waves typically have low frequency content below 10 hertz. Myopotentials from non-cardiac muscles tend to have higher frequency content, in the range of 80 hertz and above. P-waves, which tend to be discarded or considered undesirable, appear at frequencies in the 30-60 hertz range. R-waves, which are often used as the benchmark for beat detection, have frequency content in the range of 20-40 hertz.

Making detection more difficult is the fact that the cardiac conditions which an implanted device must accurately detect are abnormal conditions. In particular, various tachyarrhythmia conditions may occur. Some, but not all, tachyarrhythmia conditions are malignant. In some morphologies, R-waves become difficult to discern, particularly with automated detection techniques. Improvements allowing for better detection, particularly during tachyarrhythmia conditions, are desired.

SUMMARY

The present invention, in illustrative embodiments, includes methods and devices for analyzing cardiac signals in an implantable cardiac stimulus system. Within the analysis, a threshold may be defined related to a cardiac event rate. If the cardiac event rate does not exceed the threshold, filtering of captured cardiac signals occurs, including filtering of certain low frequency signal components, likely to correspond to T-wave signals, by the use of high pass filtering. If the cardiac event rate does exceed the threshold, the high pass filter for T-wave signals is bypassed or otherwise prevented from filtering out low frequency signal components. In an illustrative example, T-wave filtering may occur in the range of 10 hertz to prevent oversensing of the T-wave during beat detection. In another example, the T-wave filtering occurs as part of separate filtering from DC filtering of an input signal. In some embodiments, T-wave filtering may occur in the digital domain, while DC filtering occurs in an analog domain.

DETAILED DESCRIPTION

The following detailed description should be read with reference to the drawings. The drawings, which are not necessarily to scale, depict illustrative embodiments and are not intended to limit the scope of the invention.

As used herein, the phrase "attenuating T-waves" refers to frequency selective attenuation that reduces the relative weight of frequency components typically associated with T-waves. Actual T-waves may or may not be attenuated by such filtering, as the T-wave may not always be discernable among received signals. At times, the received signal may not contain a T-wave because the received signal does not represent a cardiac event, meaning the received signal will likely be rejected by beat detection methods performed on filtered and conditioned received signals.

Figure 2:
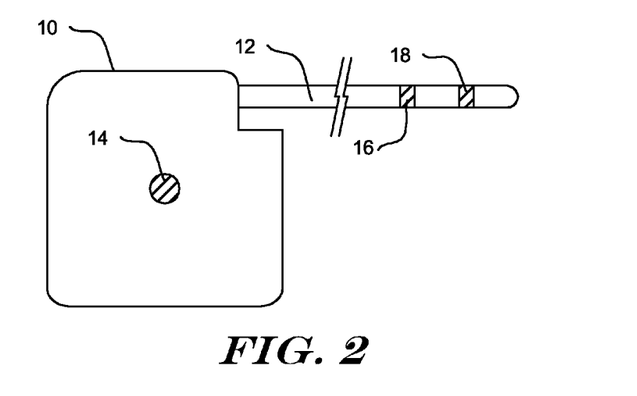
FIG. 2 is a perspective diagram of an implantable cardiac stimulus device.

An example implantable cardiac stimulus device is shown in FIG. 2. A canister 10 houses operational circuitry, batteries, etc. for operating the device. A lead 12 extends from the device. A canister electrode 14 is shown, along with lead electrodes 16, 18. The number, placement and type of electrodes may vary, as may the size of the canister and lead. The stimulus device may be configured for providing pacing functions, defibrillation functions, or both. The cardiac stimulus device may be implanted in a patient in a suitable fashion. In some embodiments, this will mean implantation including electrode insertion into the heart, on the heart, or through blood vessels. Other embodiments may include subcutaneous implantation. Examples of methods and devices for, and associated with, subcutaneous placement are illustrated in U.S. Pat. Nos. 6,788,974; 6,754,528; 6,721,597; and 6,647,292, the disclosures of which are all incorporated herein by reference.

Figure 3:
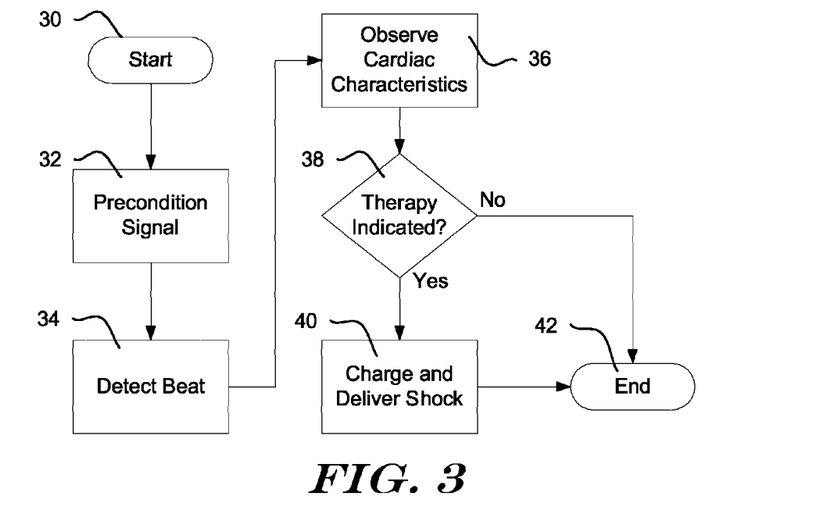
FIG. 3 shows, in block form, an illustrative method of cardiac monitoring and stimulus.

FIG. 3 shows, in block form, an illustrative method of cardiac monitoring and stimulus. From a start block 30, the method begins with steps of capturing and preconditioning cardiac signals, as shown at 32, which is performed using implanted electrodes. For example, a pair of electrodes chosen from electrodes 14, 16, 18 (FIG. 1) may be selected to capture a cardiac signal. The signal may be filtered to exclude various known noise sources. For example, if the R-wave is desired, a bandpass filter (which may have first and second filter sections) may be used to allow only signals having desired frequencies to pass. The signal may also be amplified in one or more stages during step 32. The signal preconditioning step 32 may include both analog and digital operations as well as analog-to-digital conversion.

The method may also include detecting a beat or other cardiac event, as shown at 34. Next, cardiac characteristics are observed, as shown at 36. This may include observing a beat or event rate, or may include more sophisticated analysis of signal morphology. Some illustrative examples of beat morphology analysis are shown in copending U.S. application Ser. No. 10/856,084, filed May 27, 2004, entitled METHOD FOR DISCRIMINATING BETWEEN VENTRICULAR AND SUPRAVENTRICULAR ARRHYTHMIAS, now U.S. Pat. No. 7,330,757, the disclosure of which is incorporated herein by reference.

From the observed cardiac characteristics, it is then determined whether therapy is indicated, as shown at 38. If so, then a shock is delivered, as shown at 40. Shock delivery may include steps of charging a capacitor or set of capacitors to a desired stimulus level and delivering a shock to the patient via a pair of electrodes. If no therapy is indicated, or after therapy is delivered, the method ends as shown by end block 42.

Figure 4:
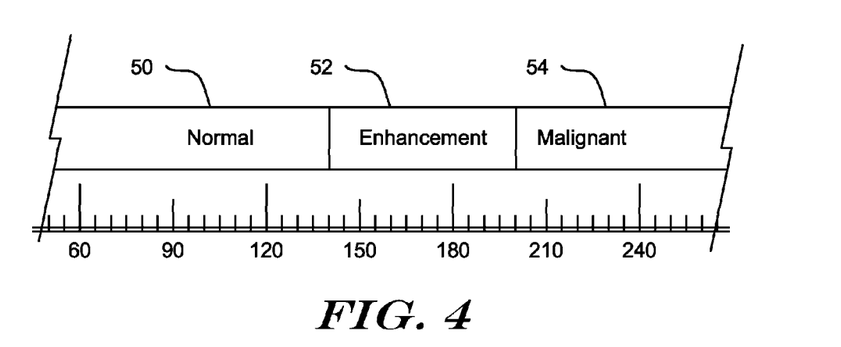
FIG. 4 shows beat ranges for an illustrative cardiac monitoring and stimulus method.

FIG. 4 shows beat ranges for an illustrative cardiac monitoring and stimulus method. At the bottom of FIG. 4 is an illustrative indication of beat rate, with a range of 60-240 beats per minute (bpm) shown. As illustrated, three beat ranges have been identified. A normal range 50 extends up to about 140 bpm. For the illustrative system, cardiac rhythms occurring in this range are not further analyzed, as they are presumed healthy. An enhancement zone 52 is also shown, including a range from 140 to 200 bpm. Cardiac rhythms classified in this zone are analyzed to determine whether the elevated event rate is indicative of a malignant condition, an abnormal condition, or simply patient activity. A zone above 200 bpm is labeled as a malignant zone 54. Cardiac rhythms at this high rate may be considered malignant and are therefore treated with electrical stimulus, in the illustrative embodiment.

The actual boundaries of the zones 50, 52, 54 may vary depending on individual patients. One or more zones 50, 52, 54 may be omitted in some embodiments. In some embodiments, only the normal zone 50 and enhancement zone 52 are included, wherein cardiac rhythms in the enhancement zone are analyzed in detail, but no beat rates automatically qualify for stimulus. Other embodiments may exclude the enhancement zone 52, with detailed analysis of beat morphology excluded. Yet other embodiments may exclude a normal zone, with cardiac event morphology analyzed continuously.

In some embodiments the distinction between analysis of a cardiac rhythm and non-analysis of a cardiac rhythm rests largely in the use of a template for comparison to captured beats. In other embodiments, "analyzed" beats or events may be recorded and stored. These steps of recording and storing, as well as comparison to a template, typically increase power consumption. The use of several zones including a "normal" zone 50, therefore, can reduce power consumption when the patient is experiencing a cardiac rhythm that is unlikely to be tachyarrhythmic and/or malignant.

Figure 5:
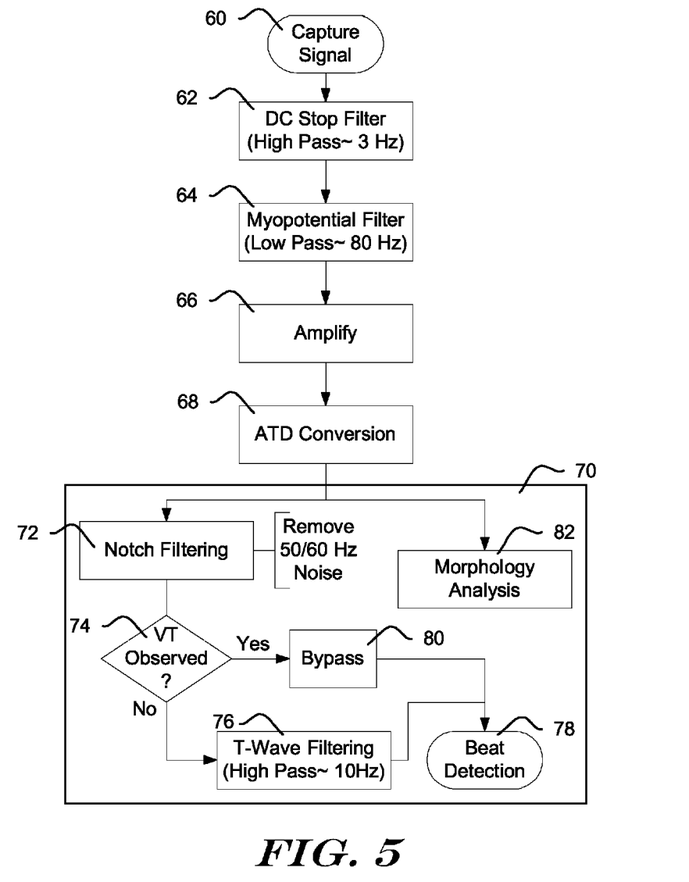
FIG. 5 shows, in block form, an illustrative method of signal analysis.

FIG. 5 shows, in block form, an illustrative method of signal analysis. A signal is captured, as shown at 60, and subjected to DC filtering, as shown at 62, followed by filtering for myopotentials and other high frequency signals, as shown at 64. The illustrative corner frequencies at 3 Hz and 80 Hz may be modified as desired, and are shown quantitatively for purely illustrative reasons.

The preconditioned signal is also amplified, as shown at 66, and undergoes analog-to-digital conversion, as shown at 68. The filtering and amplification steps are shown in an illustrative order that may be suitable modified in a number of ways. In some embodiments, filtering and amplification steps may also be combined.

After analog-to-digital conversion at 68, the signal enters the digital domain as indicated by box 70, and remains there. In a first branch of analysis, the digitized signal undergoes digital filtering via a notch filter, as shown at 72. This filtering may remove 50/60 Hz noise, as indicated. Because digital domain filtering allows very sharp attenuation characteristics, digitally filtering 50/60 Hz noise may be preferable. If desired, and in some embodiments, 50/60 Hz filtering may be implemented in the analog domain instead.

After notch filtering, it is determined whether a tachyarrhythmia has been detected, as shown at 74. If not, the signal undergoes T-wave directed filtering, as shown at 76. In the illustrative example, T-waves are digitally filtered using a filtering scheme having a corner frequency at about 10 Hz, as indicated, though a corner frequency may be used. It should be noted that this filtering, in the digital domain, may be executed by any of a variety of known digital filtering approaches. The signal then passes to beat detection analysis, as shown at 78. Going back, if a tachycardia is observed at 74, the filtering at 76 is bypassed, as indicated at 80.

Often a tachyarrhythmic condition is at least partly characterized by a reduction, delay, or elimination of the T-wave. Some patients' signal morphology during a tachyarrhythmia loses the T-wave. If the T-wave is not being generated in the usual manner or with its usual amplitude, filtering it becomes somewhat unnecessary. Further, given a tachyarrhythmia is occurring, the cardiac signal may already be corrupted or noise dominated, irregular, or otherwise difficult to analyze. Frequency content of the R-wave may change from that which is ordinarily observed, as shown in FIG. 1. Thus, retaining a greater portion of the original signal may aid in beat detection.

Morphology analysis 82 is shown illustratively as occurring outside of the beat detection process including filtering at 72 and 76, beat detection 78, and bypass 80. The morphology analysis 82 may instead occur after notch filtering 72 to remove 50/60 Hz noise, if desired.

Figure 6:
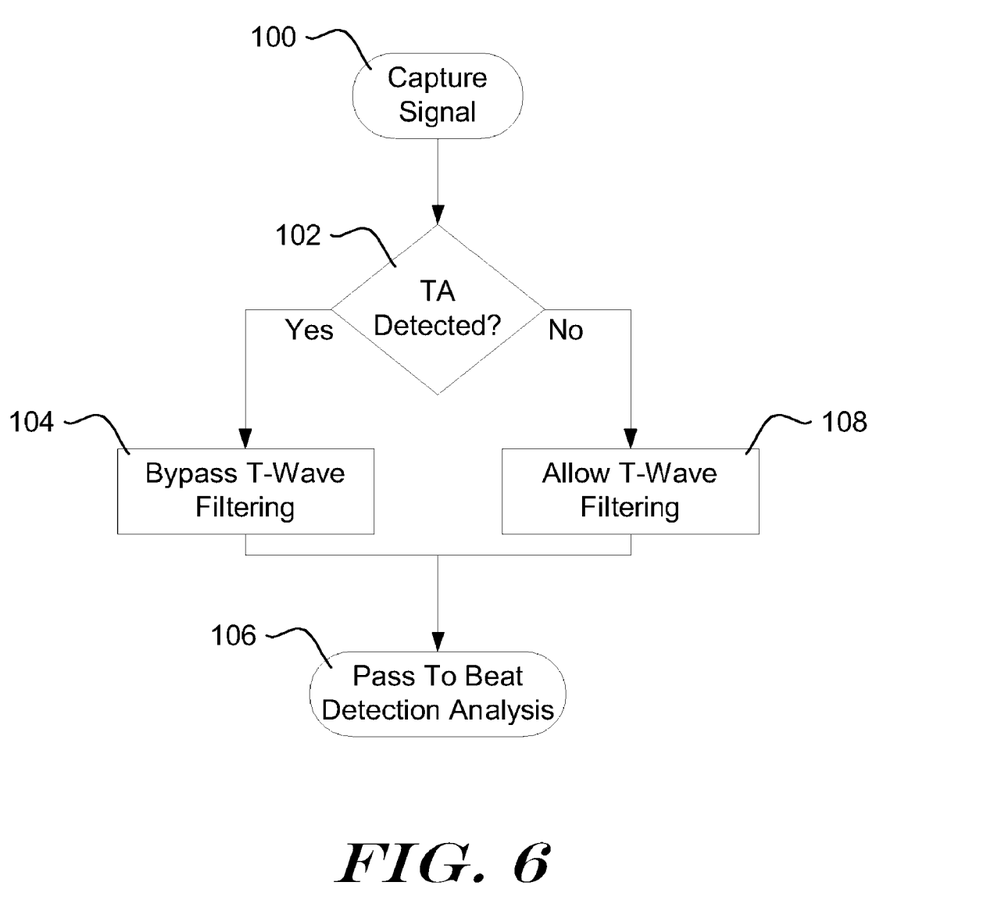
FIG. 6 shows, in block form, another illustrative method of signal analysis.

FIG. 6 shows, in block form, another illustrative method of signal analysis. After signal capture, shown at 100, it is determined whether a tachyarrhythmia has been detected, as shown at 102. Whether a tachyarrhythmia has been detected will depend upon the characteristics of the patient's cardiac rhythm as determined by observation of prior cardiac events. If a tachyarrhythmia has been detected, T-wave filtering is bypassed, as shown at 104. The signal then passes to detection analysis, as noted as 106. If no tachyarrhythmia is detected, T-wave filtering occurs, as shown at 108, and the signal is passed to detection analysis. This simplified example omits various signal conditioning steps that may be performed prior to, in association with, or after the steps shown, as those steps may vary widely.

Figure 7:
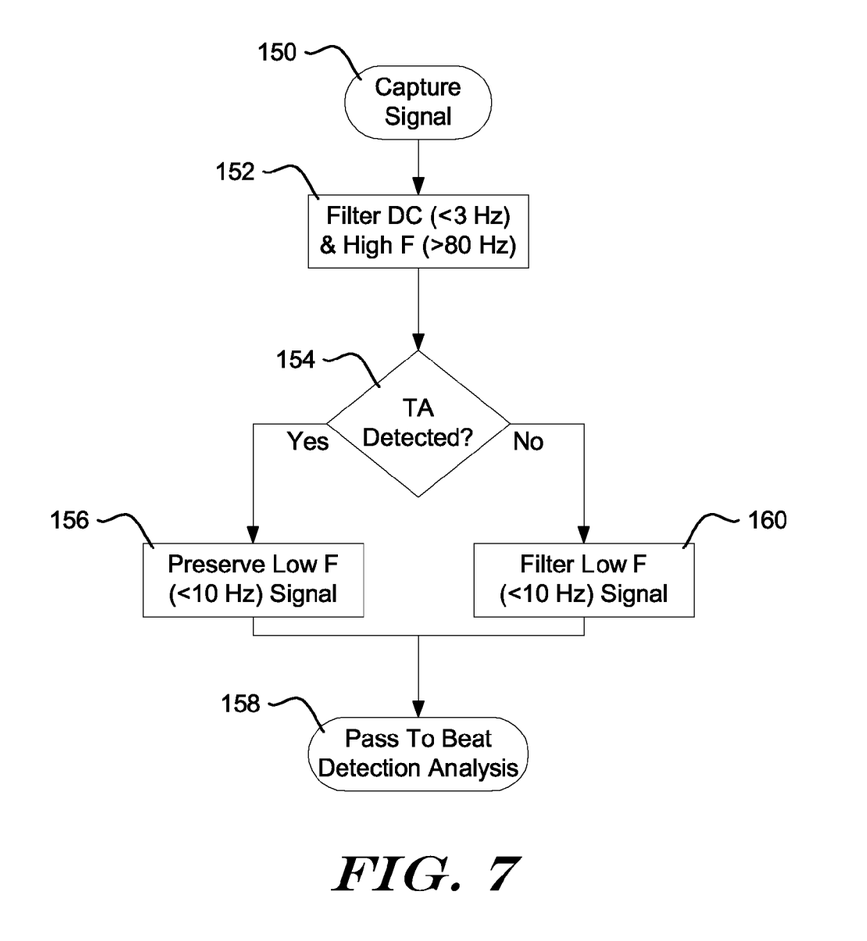
FIG. 7 shows, in block form, an illustrative method of signal analysis.

FIG. 7 shows, in block form, an illustrative method of signal analysis. This example includes greater detail than in FIG. 6. After signal capture, shown at 150, DC and high frequency components of the signal are filtered, as shown at 152. Example corner frequencies for such filtering are given at 3 Hz for DC and 80 Hz for high frequency; these corner frequencies may be changed as desired. Next it is determined whether a tachyarrhythmia has been detected, as shown at 154. If so, low frequency components of the signal, illustratively indicated as below 10 Hz, are preserved, as shown at 156, and the signal is passed to beat detection analysis as shown at 158. Otherwise, low frequency components, in the range of T-waves, are filtered, as shown at 160, and the signal is passed for analysis as shown at 158. Again, the illustrative example shows low frequency filtering in the range of 10 Hz, though this corner frequency may be set as desired.

Figure 8A:
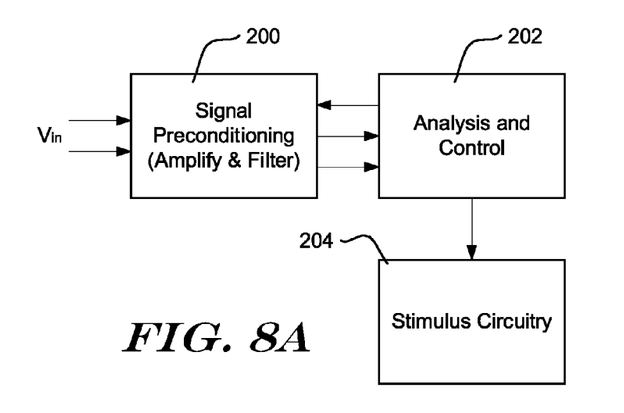
FIGS. 8A-8B are block diagrams for an implantable cardiac stimulus device.

FIG. 8A is a block diagram for an implantable cardiac stimulus device. An amplification/filter block 200 is shown as receiving a captured voltage, $V_{in}$, which may be sensed using any suitable electrode configuration. $V_{in}$ is modified in block 200 and passed on to analysis/control block 202, where the signal may be, for example, converted to digital form and used in a number of analytical processes. If desired, block 200 and portions of block 202 may be provided on an analog chip, while other portions of block 202 that are suited for digital analysis of the signal may be provided on a separate digital chip. As shown, block 202 exerts control over block 200. Block 202 is also coupled to stimulus circuitry 204.

A control signal from block 202 to block 200 may include signals indicating the timing of sampling of received signals, if desired. In accordance with some embodiments of the present invention, the control signal from block 202 to block 200 includes a signal controlling whether $V_{in}$ is subjected to analog high-pass filtering in addition to any DC filtering that occurs.

Figure 8B:
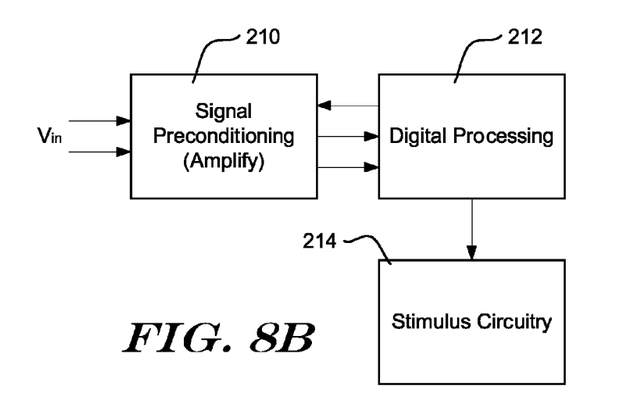

FIG. 8B is another block diagram for an implantable cardiac stimulus device. The illustrative device includes a signal preconditioning block 210 which performs amplification and sends a signal $V_{in}$ to a digital processing block 212. The digital processing block 212 may perform at least some of the filtering functions digitally, in contrast to the embodiment shown in FIG. 8A. The digital processing block 212 may include a controller, microcontroller, digital signal processor, or the like. Analog-to-digital conversion may take place in the signal conditioning block 210, or may be part of the digital processing block 212. The digital processing block 212 may, as shown, issue control signals to the signal conditioning block 210, for example, to control the amplification gain. The digital processing block 212 also issues commands for stimulus circuitry 214.

As illustrated in the examples of FIGS. 8A-8B, various filtering functions may occur in either the analog or digital domain. The methods, devices and systems encompassed by the present invention may include various configurations for such functionality. The specifics of the example in FIG. 5 are merely illustrative of one way that the present invention may be practiced, and the present invention is not limited to the configuration shown in that illustrative example.

Figure 9A:
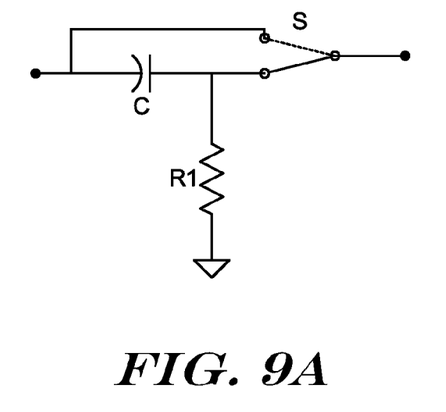
FIG. 9A illustrates a circuit having a switch placed relative a high pass filter.

FIG. 9A illustrates a circuit configuration having a switch placed relative to a high pass analog filter. Additional filters, such as a DC-stopping filter circuit and a filter for attenuating myopotentials and high frequency noise are omitted in FIG. 9A. FIG. 9A illustrates a high pass filter comprising capacitor C and resistor R1. Switch S is shown across the filter. When switch S is in the position shown, the circuit operates as a high pass filter. When switch S is in the position shown in phantom, the filter is bypassed. In this fashion, switch S operates to short across the low-frequency attenuating element of the circuit, the series capacitor C. The values of the capacitor C and resistor R1 may be selected to place the filter pole at a desired frequency. The switch S may be controlled in response to a control signal generated relative to whether a tachyarrhythmia has been sensed.

Figure 9B:
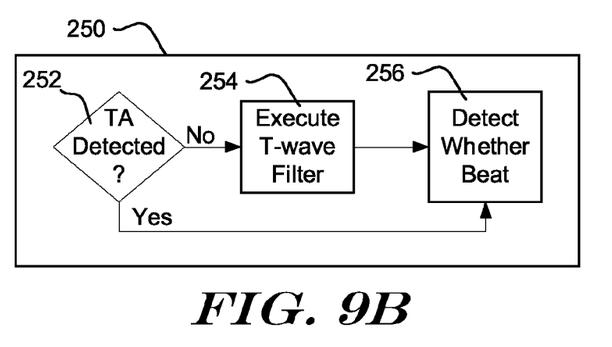
FIG. 9B illustrates digital domain treatment of filter bypass in an illustrative embodiment of the present invention.

FIG. 9B illustrates digital domain treatment of filter bypass in an illustrative embodiment of the present invention. The example in FIG. 9B may be embodied, for example, in executable instructions for a processor, microprocessor, controller, DSP, or the like. A software module 250 includes a first step of determining whether a tachyarrhythmia has been detected, as shown at 252. If not, the software module 250 executes a T-wave filter, using a digital filter such as a recursive digital filter or convolving digital filter, or other tool for digital filtering. The signal is then treated to beat detection as shown at 256. If a tachyarrhythmia is detected at 252, the software module 250 skips T-wave filtering at 254 and goes directly to beat detection at 256.

The operational circuitry used in the implantable medical devices of the present invention may be configured to include such controllers, microcontrollers, logic devices, memory, and the like, as selected, needed, or desired for performing the steps for which each is configured. The operational circuitry may include a controller and controller readable media, the controller readable media including a controller readable instruction set for performing any of the methods discussed herein.

An illustrative embodiment of the present invention includes a method of operating an implantable cardiac stimulus device, the method comprising capturing cardiac signals between implanted electrodes, observing whether a tachyarrhythmia is likely occurring, and, if not, filtering a portion of a cardiac signal to attenuate T-waves and using the filtered portion of the cardiac signal to detect whether a cardiac event has occurred. In the illustrative embodiment, if a tachyarrhythmia is occurring, the method may include not attenuating the T-waves in the cardiac signal and using the unfiltered portion of the cardiac signal to detect whether a cardiac event has occurred. The step of analyzing the cardiac signals may include observing a rate of cardiac events and, if the rate exceeds at least a first threshold, it is determined that a tachyarrhythmia is occurring. In some embodiments, the T-waves are attenuated in the digital domain and, if no tachyarrhythmia is likely occurring, a portion of an instruction set for digital filtering is bypassed to avoid digitally attenuating the T-waves. In other embodiments, the T-waves are attenuated in the analog domain and, if no tachyarrhythmia is likely occurring, a portion of an analog circuit is bypassed to avoid analog attenuation of the T-waves.

In another embodiment of the method, a first threshold event rate and a second threshold event rate are defined, the step of analyzing the cardiac signals includes estimating a cardiac event rate, if the cardiac event rate exceeds the first threshold event rate but not the second threshold event rate, it is determined that a tachyarrhythmia is occurring, or, if the cardiac event rate exceeds the second threshold event rate, it is determined that treatment stimulus is indicated. The step of analyzing the cardiac signals to determine whether a tachyarrhythmia is likely occurring may include analyzing the morphology of at least one cardiac signal. The methods may further comprise analyzing the cardiac signals to determine whether a malignant cardiac condition indicating treatment is likely occurring and, if so, delivering cardioversion/defibrillation stimulus. An illustrative embodiment also includes filtering DC components of the captured signal.

Another illustrative embodiment includes an implantable cardiac stimulus device system comprising electrodes for capturing cardiac signals, and operational circuitry for receiving the cardiac signals from the electrodes, the operational circuitry adapted evaluate cardiac signals to detect cardiac events and further adapted to determine whether a patient's cardiac beat rate exceeds a threshold. In this illustrative embodiment, the operational circuitry may attenuate T-waves of the cardiac signals prior to cardiac event detection if the beat rate does not exceed the threshold, and the operational circuitry does not attenuate T-waves of the cardiac signals prior to cardiac event detection if the beat rate exceeds the threshold. The operational circuitry may include a digital processor programmed to calculate a cardiac beat rate for the patient, compare the rate to the threshold, and digitally attenuate the T-waves of the cardiac signals if the beat rate does not exceed the threshold. The operational circuitry may comprise analog T-wave filtering components adapted to perform analog attenuation of the T-waves and the operational circuitry comprises a switch to bypass the analog T-wave filtering components if the beat rate exceeds the threshold. The device may include high power capacitors and charging circuitry for charging the high power capacitors to levels appropriate for cardioversion and/or defibrillation.

Yet another illustrative embodiment includes an implantable cardiac stimulus device comprising a canister housing operational circuitry, the operational circuitry configured to perform the steps of: receiving cardiac signals captured using implanted electrodes; observing whether a tachyarrhythmia is likely occurring; and if not, filtering a portion of a cardiac signal to attenuate T-waves and using the filtered portion of the cardiac signal to detect whether a cardiac event has occurred; or, if so, not attenuating the T-waves in the cardiac signal and using the unfiltered portion of the cardiac signal to detect whether a cardiac event has occurred.

The operational circuitry may be configured such that the step of analyzing the cardiac signals includes observing a rate of cardiac events and, if the rate exceeds at least a first threshold, it is determined that a tachyarrhythmia is occurring. The operational circuitry may be configured such that the T-waves are attenuated in the digital domain and, if no tachyarrhythmia is likely occurring, a portion of an instruction set for digital filtering is bypassed to avoid digitally attenuating the T-waves. The operational circuitry may be configured such that the T-waves are attenuated in the analog domain and, if no tachyarrhythmia is likely occurring, a portion of an analog circuit is bypassed to avoid analog attenuation of the T-waves.

In another embodiment, the operational circuitry is configured such that a first threshold event rate and a second threshold event rate are defined, a cardiac event rate is estimated, if the cardiac event rate exceeds the first threshold event rate but not the second threshold event rate, it is determined that a tachyarrhythmia is occurring, and if the cardiac event rate exceeds the second threshold event rate, it is determined that treatment stimulus is indicated. The operational circuitry may be configured to perform the steps of analyzing the cardiac signals to determine whether a malignant cardiac condition indicating treatment is likely occurring and, if so, delivering cardioversion/defibrillation stimulus. The operational circuitry may be configured to filter DC components of the received cardiac signals. The operational circuitry may include high power capacitors and charging circuitry for charging the high power capacitors to levels appropriate for cardioversion and/or defibrillation.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable cardiac stimulus device (ICSD) system comprising:
    electrodes for capturing cardiac signals; and
    operational circuitry for receiving the cardiac signals from the electrodes, the operational circuitry configured to:
    evaluate cardiac signals to detect cardiac events;
    calculate a cardiac beat rate based on detected cardiac events; and
    determine whether a patient's cardiac beat rate exceeds a threshold;
    wherein the operational circuitry is also configured to apply filtering to the cardiac signals comprising a first filtering mode and a second filtering mode, wherein the first filtering mode attenuates T-waves of the cardiac signals prior to cardiac event detection more than the second filtering mode, and
    the operational circuitry is configured to determine whether the cardiac beat rate exceeds the threshold and, in response:
        to select and apply the first filtering mode if the cardiac beat rate does not exceed the threshold; and
        to select and apply the second filtering mode if the cardiac beat rate exceeds the threshold.

2. The ICSD system of claim 1, wherein the operational circuitry includes a digital processor programmed to calculate the cardiac beat rate for the patient, compare the cardiac beat rate to the threshold, and apply the first filtering mode to digitally attenuate the T-waves of the cardiac signals if the cardiac beat rate does not exceed the threshold.

3. The ICSD system of claim 1, wherein the operational circuitry comprises analog T-wave filtering components adapted to perform analog attenuation of the T-waves and the operational circuitry comprises a switch for applying the first and second filtering modes by either:
    applying the first filtering mode by directing cardiac signal to the analog T-wave filtering components; or
    applying the second filtering mode by allowing cardiac signal to bypass the analog T wave filtering components.

4. The ICSD system of claim 1, wherein the operational circuitry includes high power capacitors and charging circuitry for charging the high power capacitors to levels appropriate for cardioversion and/or defibrillation.

5. An implantable cardiac stimulus device comprising a canister housing operational circuitry, the operational circuitry configured to perform the steps of:
    receiving cardiac signals captured using implanted electrodes;
    detecting cardiac events in the cardiac signals; and
    determining whether a tachyarrhythmia is likely occurring;
    wherein the operational circuitry is further configured to apply one of first or second filtering modes to the received cardiac signals before detecting a cardiac event in the cardiac signals, wherein the first filtering mode is configured to attenuate T-waves and the second filtering mode is configured to attenuate T-waves less than the first filtering mode, wherein:
        if the operational circuitry determines that no tachyarrhythmia is likely occurring, the operational circuitry is configured to select and apply the first filtering mode, and
        if the operational circuitry determines that a tachyarrhythmia is likely occurring, the operational circuitry is configured to select and apply the second filtering mode,
    such that if the operational circuitry observes an onset of tachyarrhythmia, the operational circuitry will switch from the first filtering mode to the second filtering mode while the tachyarrhythmia is occurring.

6. The device of claim 5, wherein the operational circuitry is configured such that the step of determining whether a tachyarrhythmia is likely occurring includes calculating a rate of cardiac events and, if the rate exceeds at least a first threshold, concluding that a tachyarrhythmia is likely occurring.

7. The device of claim 5, wherein the operational circuitry is configured to apply the first or second filtering modes in the digital domain and, when applying the second filtering mode, a portion of an instruction set for digital filtering is bypassed to avoid filtering to digitally attenuate T-waves.

8. The device of claim 5, wherein the operational circuitry is configured to apply the first or second filtering modes in the analog domain and, when applying the second filtering mode, a portion of an analog circuit is bypassed to avoid analog filtering to attenuate T-waves.

9. The device of claim 5, wherein the operational circuitry is configured to:
define a first threshold event rate and a second threshold event rate;
estimate a cardiac event rate; and, at any given time, one of:
determine that no tachyarrhythmia is occurring if the cardiac event rate does not exceed the first threshold event rate;
determine that a tachyarrhythmia is occurring if the cardiac event rate exceeds the first threshold event rate but not the second threshold event rate; or
determine that a tachyarrhythmia is likely occurring and therapy stimulus is needed if the cardiac event rate exceeds the second threshold event rate.

10. The device of claim 5, wherein the operational circuitry is configured to analyze the received cardiac signals to determine whether a malignant cardiac condition indicating treatment is likely occurring and, if so, deliver cardioversion/defibrillation stimulus.

11. The device of claim 5, wherein the operational circuitry is configured to filter DC components of the received cardiac signals.

12. The device of claim 5, wherein the operational circuitry includes high power capacitors and charging circuitry for charging the high power capacitors to levels appropriate for cardioversion and/or defibrillation.

13. An implantable medical device comprising a canister housing operational circuitry and a plurality of electrodes coupled to the operational circuitry, the operational circuitry being configured to:
receive cardiac signals from the plurality of electrodes;
detect cardiac events in the received cardiac signals;
determine whether a tachyarrhythmia is likely occurring;
wherein the operational circuitry comprises means for filtering the received cardiac signals, the means for filtering being configurable in response to determining whether a tachyarrhythmia is likely occurring such that first and second filtering modes are provided to filter the received cardiac signals in order to detect cardiac events in the received cardiac signals,
wherein the first filtering mode is configured to attenuate T-waves and the second filtering mode is configured to attenuate T-waves less than the first filtering mode, and
wherein the operational circuitry is configured to perform as follows:
in response to determining that no tachyarrhythmia is likely occurring, configuring the means for filtering to apply the first filtering mode;
in response to determining that a tachyarrhythmia is likely occurring, configuring the means for filtering to apply the second filtering mode.

14. The implantable medical device of claim 13 further comprising stimulus output circuitry configured for providing therapeutic stimulus in response to a condition requiring treatment, wherein the stimulus output circuitry includes a capacitor system.

15. The implantable medical device of claim 13 wherein the means for filtering comprises a digital filter.

16. The implantable medical device of claim 13 wherein the means for filtering comprises analog circuitry including at least a bypass switch relative to a high pass filter, wherein the bypass switch is operable to select the first filtering mode or the second filtering mode.

* * * * *

UNITED STATES PATENT AND TRADEMARK OFFICE
CERTIFICATE OF CORRECTION

| | | |
|---|---|---|
| PATENT NO. | : 8,666,489 B2 | Page 1 of 1 |
| APPLICATION NO. | : 13/358015 | |
| DATED | : March 4, 2014 | |
| INVENTOR(S) | : Alan H. Ostroff | |

It is certified that error appears in the above-identified patent and that said Letters Patent is hereby corrected as shown below:

In the Claims

In column 8, line 21, In Claim 3, delete "T -wave" and insert --T-waves--, therefor In column 8, line 28, In Claim 3, delete "T wave" and insert --T-waves--, therefor In column 10, line 2, In Claim 13, after "signals;", insert --and--, therefor Signed and Sealed this
Seventeenth Day of June, 2014

Michelle K. Lee
*Deputy Director of the United States Patent and Trademark Office*